United States Patent
Lu et al.

(10) Patent No.: US 10,582,893 B2
(45) Date of Patent: Mar. 10, 2020

(54) FINGER CLAMPING DEVICE AND OXIMETER USING THE SAME

(71) Applicant: Hangzhou Jiangyu Innovation Medical Technology CO., LTD, Hangzhou (CN)

(72) Inventors: Zhan-Sheng Lu, Shenzhen (CN); Yu-Feng Zhang, Shenzhen (CN)

(73) Assignee: Hangzhou Jiangyu Innovation Medical Technology CO., LTD, Hangzhou (CN)

(*) Notice: Subject to any disclaimer, the term of this patent is extended or adjusted under 35 U.S.C. 154(b) by 270 days.

(21) Appl. No.: 15/603,485

(22) Filed: May 24, 2017

(65) Prior Publication Data
US 2017/0340281 A1    Nov. 30, 2017

(30) Foreign Application Priority Data
May 24, 2016 (CN) .......................... 2016 1 0351772

(51) Int. Cl.
*A61B 5/00* (2006.01)
*A61B 5/1455* (2006.01)

(52) U.S. Cl.
CPC ........ *A61B 5/6838* (2013.01); *A61B 5/14552* (2013.01); *A61B 5/6826* (2013.01); *A61B 2562/0238* (2013.01)

(58) Field of Classification Search
CPC . A61B 5/6838; A61B 5/14552; A61B 5/6826; A61B 2562/0238
See application file for complete search history.

(56) References Cited

U.S. PATENT DOCUMENTS

| 4,685,464 A | * | 8/1987 | Goldberger ........ A61B 5/14552 600/344 |
| 6,654,621 B2 | * | 11/2003 | Palatnik ............. A61B 5/14552 600/322 |
| 7,239,905 B2 | * | 7/2007 | Kiani-Azarbayjany ..................... E02B 11/005 600/316 |
| 2012/0289800 A1 | * | 11/2012 | Isaacson .............. A61B 5/1455 600/323 |

FOREIGN PATENT DOCUMENTS

JP     2010-273976 A     12/2010

* cited by examiner

*Primary Examiner* — Eric F Winakur
*Assistant Examiner* — Abid A Mustansir
(74) *Attorney, Agent, or Firm* — ScienBiziP, P.C.

(57) ABSTRACT

An oximeter includes a main body defining an opening and a finger clamping device arranged in the opening. The finger clamping device includes a shell, an upper clamping member, and a lower clamping member. The shell includes an inner wall carrying a sliding rail. The upper clamping member is arranged in the shell and defines a spindle. A portion of the spindle is received in the sliding rail and can slide along the sliding rail. The lower clamping member faces the upper clamping member and is coupled to the upper clamping member by a torsion spring. A finger being inserted between the upper clamping member and the lower clamping member causes the torsion spring to stretch, the finger is thus clamped by the upper clamping member and the lower clamping member with an elastic restoring force.

12 Claims, 4 Drawing Sheets

FINGER CLAMPING DEVICE AND OXIMETER USING THE SAME

CROSS-REFERENCE TO RELATED APPLICATIONS

This application claims priority to Chinese Patent Application No. 201610351772.9 filed on May 24, 2016, the contents of which are incorporated by reference herein.

FIELD

The subject matter herein generally relates to medical apparatuses, and particularly to a finger clamping device and an oximeter using the same.

BACKGROUND

In medical field, an oximeter is used for measuring blood oxygen saturation of a human body and displaying pulse of a user. Generally, a finger clamping device needs to be manually pressed to clamp the finger of the user, which causes inconvenience.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
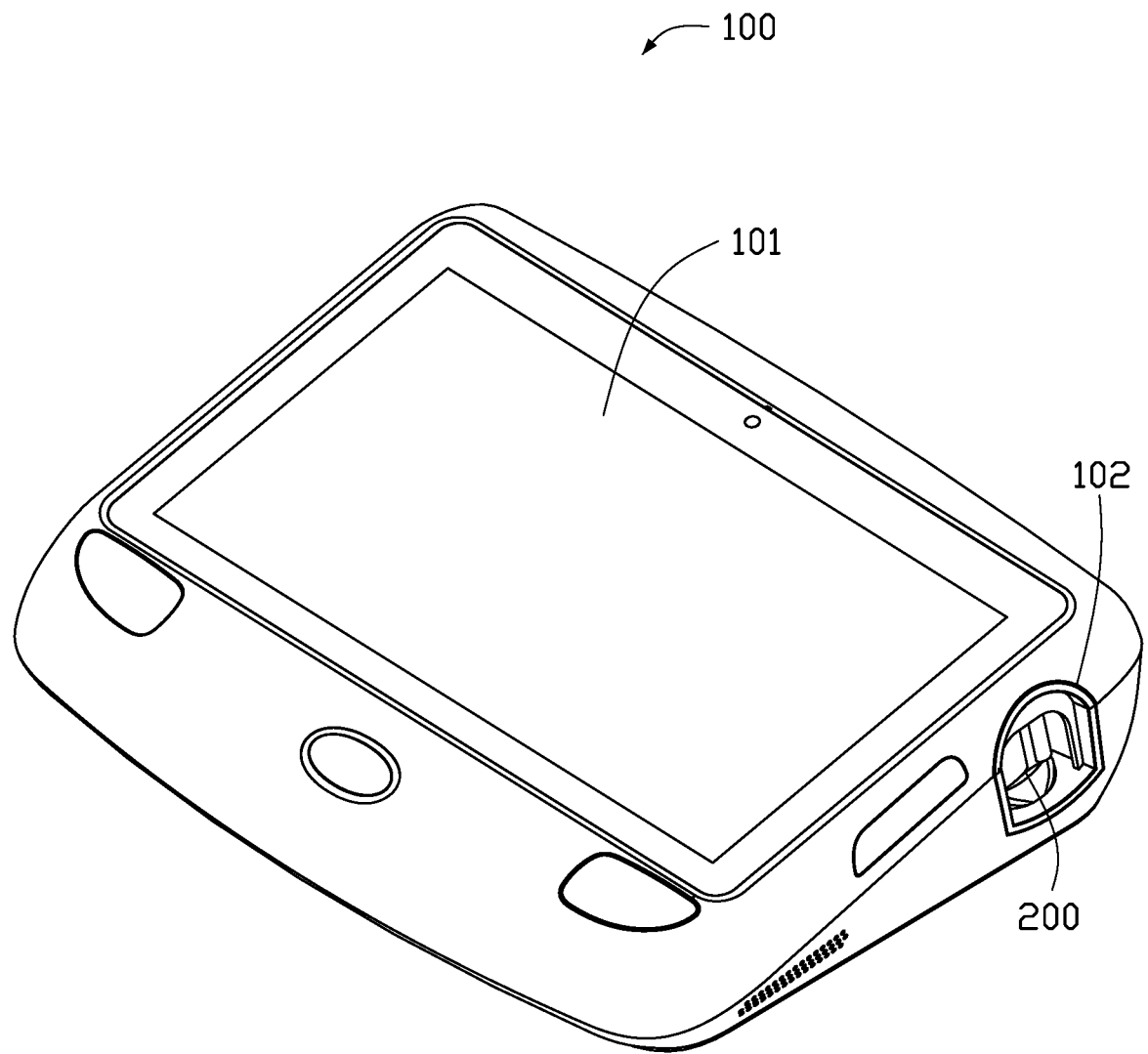
FIG. 1 is a schematic view illustrating an exemplary embodiment of an oximeter.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts have been exaggerated to better illustrate details and features of the present disclosure.

The present disclosure, including the accompanying drawings, is illustrated by way of examples and not by way of limitation. Several definitions that apply throughout this disclosure will now be presented. It should be noted that references to "an" or "one" exemplary embodiment in this disclosure are not necessarily to the same exemplary embodiment, and such references mean "at least one".

The term "comprising" means "including, but not necessarily limited to", it specifically indicates open-ended inclusion or membership in a so-described combination, group, series, and the like.

FIG. 1 illustrates an exemplary embodiment of an oximeter 100. In at least one exemplary embodiment, the oximeter 100 includes a main body 101 and a finger clamping device 200. The main body 101 defines an opening 102. The finger clamping device 200 is arranged in the opening 102. The finger clamping device 200 is used for clamping at least one finger of a user to measure blood oxygen saturation of the user. FIG. 1 illustrates only one example of the oximeter 100, another oximeter 100 can include more components than as illustrated.

Figure 2:
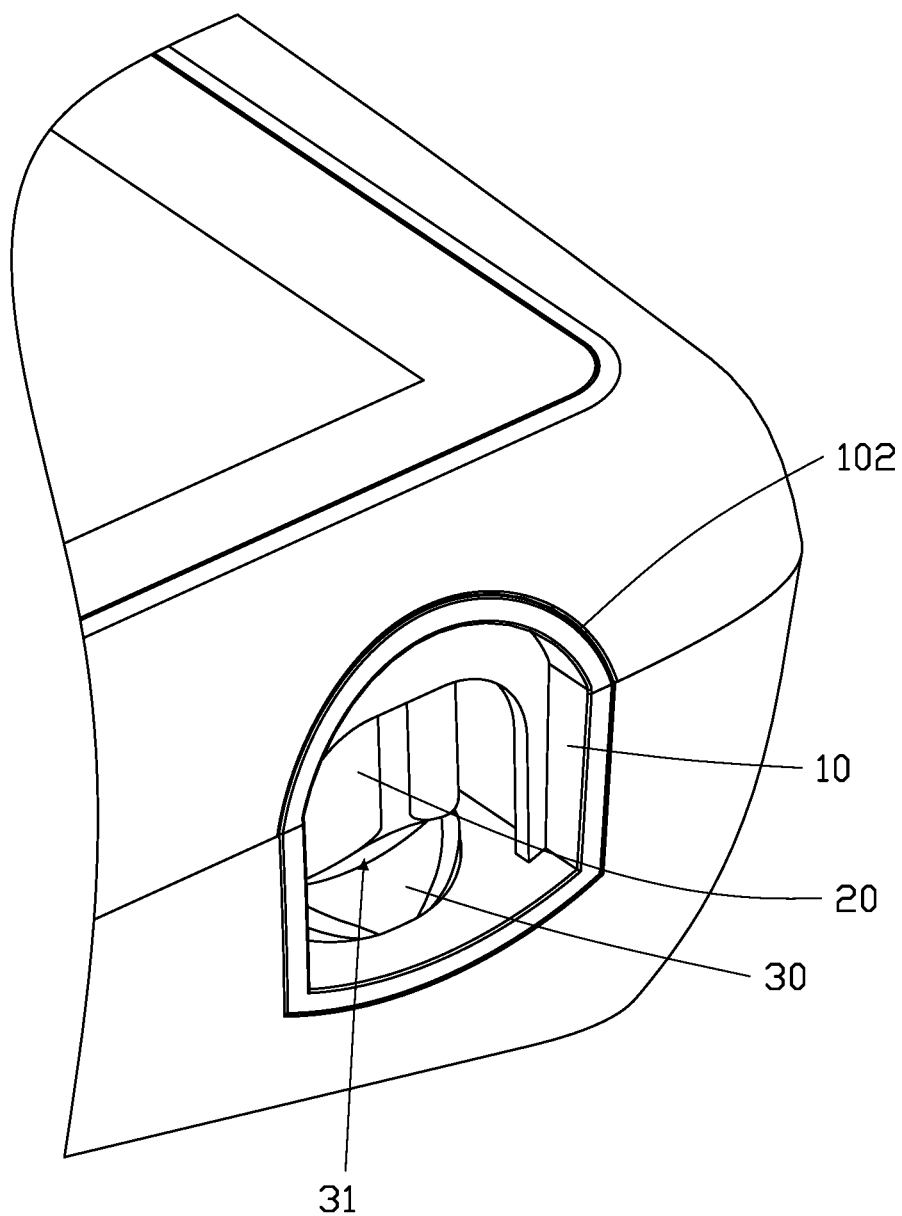
FIG. 2 is an enlarged view of a portion of the oximeter in FIG. 1.
Figure 3:
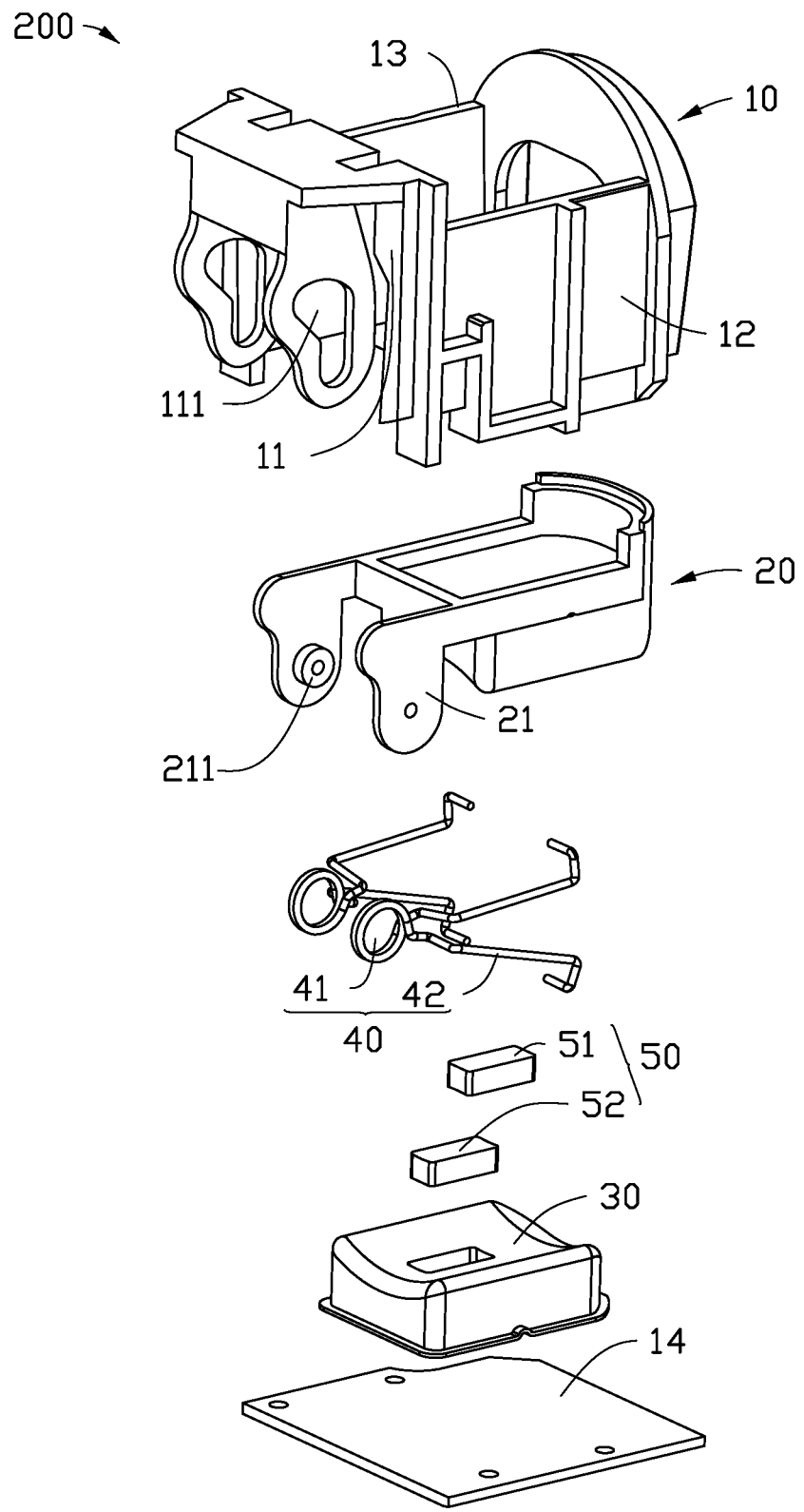
FIG. 3 is an exploded view illustrating an exemplary embodiment of a finger clamping device which can be used in the oximeter in FIG. 1.
Figure 4:
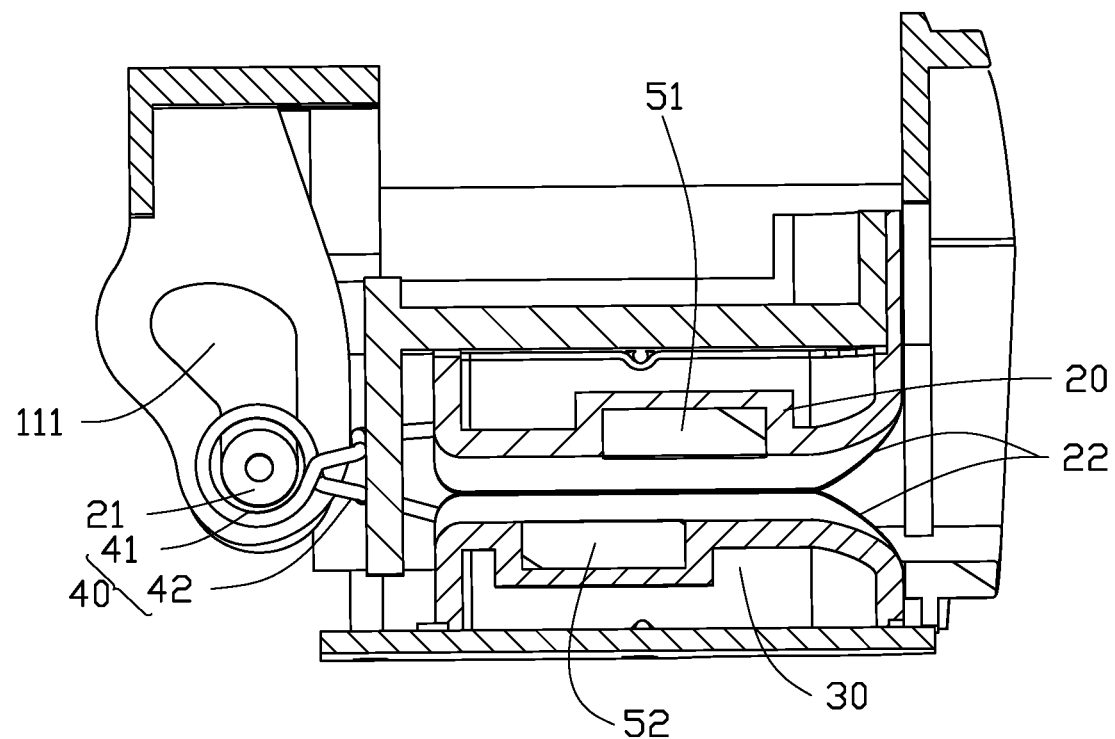
FIG. 4 is a cross-section view illustrating an exemplary embodiment of a finger clamping device which can be used in the oximeter in FIG. 1.

Referring to FIGS. 2-4, the finger clamping device 200 includes a shell 10, an upper clamping member 20, a lower clamping member 30, two torsion springs 40, and a measuring device 50.

A shape of the shell 10 matches with a shape of the opening 102. The shell 10 is received in the opening 102. In at least one exemplary embodiment, the shell 10 includes an inner wall 11, two sidewalls 12, a top surface 13, and a bottom surface 14 as shown in FIG. 3. The inner wall 11 defines two sliding rails 111.

The upper clamping member 20 and the lower clamping member 30 are arranged in the shell 10. In at least one exemplary embodiment, the upper clamping member 20 and the lower clamping member 30 are elongated members, and match with a shape of a human finger, accordingly, the finger clamping device 200 provides more comfort when clamping the finger of the user.

The lower clamping member 30 is mounted on the bottom surface 14. The upper clamping member 20 is connected to the lower clamping member 30 through the two torsion springs 40. In at least one exemplary embodiment, each torsion spring 40 includes a circle member 41 and two supporting members 42 extended from the circle member 41.

The upper clamping member 20 includes two spindles 21 extending from an end of the upper clamping member 20, each spindle 21 has a guiding rod 211 extending from the spindle 21, and the two guiding rods 211 of the upper clamping member 20 are respectively received in the sliding rails 111 and can slide or rotate along the sliding rails 111.

The circle member 41 is sheathed on the guiding rod 211 and can move following the guiding rod 211. The two supporting members 42 are respectively mounted on inner surface of one sidewall of the upper clamping member 20 and the lower clamping member 30. In a natural state, the upper clamping member 20 and the lower clamping member 30 is in contact with each other under an elastic force of the torsion spring 40.

In at least one exemplary embodiment, two opposite sides of the upper clamping member 20 and the lower clamping member 30 each define an inclined surface 22. The inclined surface 22 of the upper clamping member 20 and the inclined surface 22 of the lower clamping member 30 are arranged away from the inner wall 11 and are oppositely facing, thus, an opening 31, as shown in FIG. 2, is formed between the upper clamping member 20 and the lower clamping member 30. In at least one exemplary embodiment, the opening 31 is trumpet-shaped, thus, the opening 31 enables the finger of the user to be conveniently and comfortably inserted into the finger clamping device 200.

In at least one exemplary embodiment, the upper clamping member 20 and the lower clamping member 30 can be made from plastic or rubber material.

The measuring device 50 is arranged in the finger clamping device 200, the measuring device 50 is used for measuring the blood oxygen saturation of the user. In at least one exemplary embodiment, the measuring device 50 includes an infrared transmitter 51 and an infrared receiver 52. The infrared transmitter 51 is arranged on either the upper clamping member 20 or the lower clamping member 30, the infrared receiver 52 is arranged on either the upper clamping member 20 or the lower clamping member 30. For example, the upper clamping member 20 may carry the infrared transmitter 51, and the lower clamping device 30 may carry the infrared receiver 52 or vice versa. The infrared transmitter 51 is arranged to oppositely face to the infrared receiver 52.

When the finger of the user is clamped between the upper clamping member 20 and the lower clamping device 30, the infrared transmitter 51 transmits infrared rays, the infrared receiver 52 receives the infrared rays after the infrared rays go through the clamped finger. The processor (not shown) of the oximeter 100 measures the blood oxygen saturation according to the infrared rays received by the infrared receiver 52.

When the finger of the user is inserted into the opening 31 between the upper clamping member 20 and the lower clamping member 30, the end having the inclined surface 22 of the upper clamping member 20 is driven to move away from the lower clamping member 30 by the finger. At this time, the upper clamping member 20 is driven to rotate about the guiding rod 211 of the spindle 21. When the upper clamping member 20 keeps on moving away from the lower clamping member 30, the spindle 21 slides towards the top surface 13 along the sliding rail 111. At this time, the torsion springs 40 are stretched, the finger is tightly clamped by the upper clamping member 20 and the lower clamping member 30 with an elastic restoring force of the stretched torsion springs 40, thus, the oximeter 100 can conveniently measure the blood oxygen saturation of the user.

When the finger of the user is clamped by the upper clamping member 20 and the lower clamping member 30, external light is blocked out by the shell 11, and cannot reach the measuring device 50, thereby measurements are more accurate. When the finger of the user is withdrawn from the opening 31 between the upper clamping member 20 and the lower clamping member 30, the upper clamping member 20 is driven to return to an initial position by the elastic restoring force of the torsion springs 40.

It is believed that the present embodiments and their advantages will be understood from the foregoing description, and it will be apparent that various changes may be made thereto without departing from the spirit and scope of the disclosure or sacrificing all of its material advantages, the examples hereinbefore described merely being exemplary embodiments of the present disclosure.

What is claimed is:

1. A finger clamping device comprising:
   a shell comprising an inner wall, the inner wall defining at least one sliding rail;
   an upper clamping member arranged in the shell and defining at least one spindle, wherein a portion of the spindle is received in the sliding rail, the spindle has a guiding rod, and the guiding rod is received in the sliding rail and slides or rotates along the sliding rail;
   at least one torsion spring coupled to the spindle; and
   a lower clamping member oppositely facing to the upper clamping member and coupled to the upper clamping member through the at least one torsion spring;
   wherein when a finger is inserted between the upper clamping member and the lower clamping member, the at least one torsion spring is stretched, the finger is clamped by the upper clamping member and the lower clamping member with an elastic restoring force.

2. The finger clamping device according to claim 1, wherein the upper clamping member comprises two spindles extending from an end of the upper clamping member, each spindle has the guiding rod.

3. The finger clamping device according to claim 2, wherein the torsion spring comprises a circle member and two supporting members, the circle member is sheathed on the guiding rod and moves following the guiding rod, the two supporting members are respectively mounted on inner surface of one sidewall of the upper clamping member and the lower clamping member.

4. The finger clamping device according to claim 1, wherein two opposite sides of the upper clamping member and the lower clamping member each define an inclined surface, thus, an opening is formed between the upper clamping member and the lower clamping member, the opening is used for inserting the finger.

5. The finger clamping device according to claim 1, wherein the upper clamping member and the lower clamping member are made from plastic or rubber material.

6. The finger clamping device according to claim 1, further comprising a measuring device, wherein the measuring device comprises an infrared transmitter and an infrared receiver, when the infrared transmitter is arranged on the upper clamping member, the infrared receiver is arranged on the lower clamping member, when the infrared transmitter is arranged on the lower clamping member, the infrared receiver is arranged on the upper clamping member.

7. An oximeter comprising:
   a main body defining an opening; and
   a finger clamping device arranged in the opening, the finger clamping device comprising:
   a shell comprising an inner wall, the inner wall defining at least one sliding rail;
   an upper clamping member arranged in the shell and defining at least one spindle, wherein the at least one spindle is received in the sliding rail, the at least one spindle has a guiding rod, and the guiding rod is received in the sliding rail and slides or rotates along the sliding rail;
   at least one torsion spring coupled to the spindle; and
   a lower clamping member oppositely facing to the upper clamping member and coupled to the upper clamping member through the at least one torsion spring;
   wherein when a finger is inserted between the upper clamping member and the lower clamping member, the at least one torsion spring is stretched, the finger is clamped by the upper clamping member and the lower clamping member with an elastic restoring force.

8. The oximeter according to claim 7, wherein the upper clamping member comprises two spindles extending from an end of the upper clamping member, each spindle has the guiding rod.

9. The oximeter according to claim 8, wherein the torsion spring comprises a circle member and two supporting members, the circle member is sheathed on the guiding rod and moves following the guiding rod, the two supporting members are respectively mounted on inner surface of one sidewall of the upper clamping member and the lower clamping member.

10. The oximeter according to claim 7, wherein two opposite sides of the upper clamping member and the lower clamping member each define an inclined surface, thus, an opening is formed between the upper clamping member and the lower clamping member, the opening is used for inserting the finger.

11. The oximeter according to claim 7, wherein the upper clamping member and the lower clamping member are made from plastic or rubber material.

12. The oximeter according to claim 7, further comprising a measuring device, wherein the measuring device comprises an infrared transmitter and an infrared receiver, when the infrared transmitter is arranged on the upper clamping member, the infrared receiver is arranged on the lower clamping member, when the infrared transmitter is arranged on the lower clamping member, the infrared receiver is arranged on the upper clamping member.

* * * * *